United States Patent
Sanders et al.

(10) Patent No.: US 11,865,028 B2
(45) Date of Patent: *Jan. 9, 2024

(54) SURGICAL ARM POSITIONER WITH STERILE DISPOSABLE SUPPORT

(71) Applicant: Encore Medical, LP, Austin, TX (US)

(72) Inventors: Brett Sanders, Signal Mountain, TN (US); Keith J. Harper, Hixson, TN (US)

(73) Assignee: Encore Medical, LP, Austin, TX (US)

(*) Notice: Subject to any disclaimer, the term of this patent is extended or adjusted under 35 U.S.C. 154(b) by 609 days.

This patent is subject to a terminal disclaimer.

(21) Appl. No.: 17/033,094

(22) Filed: Sep. 25, 2020

(65) Prior Publication Data

US 2021/0022907 A1    Jan. 28, 2021

Related U.S. Application Data

(63) Continuation of application No. 14/787,303, filed as application No. PCT/US2014/038072 on May 15, 2014, now Pat. No. 10,792,182.

(60) Provisional application No. 61/823,433, filed on May 15, 2013.

(51) Int. Cl.
*A61F 5/00* (2006.01)
*A61F 5/37* (2006.01)
*A61G 13/12* (2006.01)

(52) U.S. Cl.
CPC ........ *A61F 5/3761* (2013.01); *A61G 13/1235* (2013.01)

(58) Field of Classification Search
CPC ........ A61F 5/01; A61F 5/0104; A61F 5/0106; A61F 5/0109; A61F 5/0118; A61F 5/012;
(Continued)

(56) References Cited

U.S. PATENT DOCUMENTS

| 2,910,259 A | 10/1959 | Johnson |
|---|---|---|
| 4,369,774 A | 1/1983 | Robbins |

(Continued)

FOREIGN PATENT DOCUMENTS

WO    2006110671 A2    10/2006

OTHER PUBLICATIONS

International Search Report and Written Opinion in International Application No. PCT/US2014/038072, dated Sep. 16, 2014.

*Primary Examiner* — Adam Baker
(74) *Attorney, Agent, or Firm* — Veros Legal Solutions, LLP

(57) ABSTRACT

An arm retainer for supporting a patient's arm at a desired position on an articulatable support assembly secured to an operating table. The arm retainer includes a rigid arm tray (11) provided with a pair of spaced openings (16) for securement of a disposable arm support liner (10) to the tray. The arm support liner (10) is comprised of a sheet of malleable material (13) with a soft engagement surface (14) for skin contact with the patient and is provided with a predetermined cut configuration for wrapping the malleable liner (10) about the patient's arm for retention of the arm therein. The line (10) has two spaced foldout tabs (17) aligned with the corresponding tray openings (16) for securing the liner to the tray (11) by folding the tabs (17) through respective of the openings (16) and thereafter against the bottom side of the tray.

20 Claims, 6 Drawing Sheets

(58) Field of Classification Search
CPC .......... A61F 5/0123; A61F 5/013; A61F 5/05;
A61F 5/058; A61F 5/05841; A61F
5/0585; A61F 5/05858; A61F 5/37; A61F
5/3723; A61F 5/373; A61F 5/3761; A61F
5/3769; A61F 5/0584; A61F 5/05866;
A61F 5/3776; A61F 5/3784; A61F
5/3792; A61G 13/122; A61G 13/1235;
A61G 13/1245; A61G 13/124; A61G
7/05769; A61G 7/065; A61G 7/07; A61G
7/057; A61G 7/05707; A61G 7/05715;
A61G 7/05761; A61G 7/075; A61G
7/0755
USPC ....... 128/878, 874, 875, 876, 877, 881, 882,
128/845, 846; 5/600, 613, 630, 621, 623,
5/646, 647, 628
See application file for complete search history.

(56) References Cited

U.S. PATENT DOCUMENTS

| | | | |
|---|---|---|---|
| 5,136,743 A | 8/1992 | Pirela-Cruz | |
| 5,291,903 A | 3/1994 | Reeves | |
| 5,317,771 A * | 6/1994 | Cook | A61H 1/0218 128/845 |
| 5,353,809 A | 10/1994 | Faucher | |
| 5,681,268 A * | 10/1997 | Radman | A61F 5/0118 602/19 |
| 5,718,671 A | 2/1998 | Bzoch | |
| 5,785,057 A | 7/1998 | Fischer | |
| 6,629,944 B2 * | 10/2003 | Smart | A61F 5/04 5/624 |
| 8,028,702 B2 * | 10/2011 | DaSilva | A61G 13/12 128/845 |
| 8,251,879 B2 | 8/2012 | Binns et al. | |
| 8,322,342 B2 | 12/2012 | Soto et al. | |
| 8,567,839 B2 | 10/2013 | Kalus et al. | |
| 2003/0060347 A1 | 3/2003 | Tang | |
| 2004/0225241 A1 | 11/2004 | Scheinberg et al. | |
| 2005/0145255 A1 * | 7/2005 | Mengato | A61F 5/05866 128/878 |
| 2009/0293884 A1 | 12/2009 | DaSilva | |
| 2010/0018537 A1 | 1/2010 | Soto et al. | |
| 2011/0100374 A1 * | 5/2011 | Silfverskiold | A61F 5/05 128/845 |
| 2014/0026892 A1 * | 1/2014 | Drake | A61G 13/124 128/845 |

* cited by examiner

SURGICAL ARM POSITIONER WITH STERILE DISPOSABLE SUPPORT

CROSS REFERENCE

This application is a continuation of U.S. patent application Ser. No. 14/787,303, filed on Oct. 27, 2015, which is a national stage entry of PCT/US2014/038072, filed on May 15, 2014, which claims the benefit of U.S. Provisional Patent Application No. 61/823,433, filed on May 15, 2013, for SURGICAL ARM POSITIONER SUPPORT WITH STERILE DISPOSABLE SUPPORT LINER, which are hereby incorporated by reference herein in their entireties.

BACKGROUND

The present invention relates generally to a limb support and positioning structure used for maintaining a patient's arm in the desired position for surgery thereon. More specifically, the present invention relates to an operative arm support which may be articulated to suitably support an arm during surgical operations on the shoulder of an individual, such as illustrated, for example, in U.S. Pat. Nos. 8,028,702 and 8,322,342.

It is an object of the present invention to provide an arm support liner that is disposable and removably attaches to a sterile mounting tray on the distal end of an arm positioner.

SUMMARY

The arm retainer of the present invention is provided for supporting a patent's arm at a desired position on an articulatable support assembly that is secured to an operating table. The arm retainer includes a rigid arm tray having a connection stud protruding from the bottom side of the tray for connecting the tray to the articulatable support assembly. The rigid arm tray has a pair of spaced openings for securement of the disposable arm support liner to the tray. The arm support liner of the present invention is comprised of a sheet of malleable material with a soft engagement surface for contact with the patient's arm and the liner is further provided with a predetermined cut configuration for wrapping the malleable liner about the patient's arm for retention. The liner is provided with two spaced foldout tabs aligned with the tray openings for securing the liner to the tray by folding the tabs through respective of the corresponding openings and thereafter against the bottom side of the tray. After surgery, the liner is removed from the tray and disposed of, and the tray may be re-sterilized for further use. The malleable material of the liner may be malleable aluminum or lead, and the soft engagement material covering the contact surfaces of the liner may be selected as a plastic sponge foam.

The arm retainer may further include a hand grip post that extends from the top side of the support tray, and the liner of the present invention is provided with a corresponding aperture aligned with the post for passage of the post therethrough when the liner is secured to the tray. A tubular plastic sponge sleeve may be received over the post. The malleable arm support liner may further include hook and loop straps for securing the liner to the patient's arm.

BRIEF DESCRIPTION OF THE DRAWINGS

Other objects and advantages appear hereinafter in the following description and claims. The accompanying drawing show, for the purpose of exemplification, without limiting the scope of the present invention or the appended claims, certain practical embodiments of the present invention wherein:

DETAILED DESCRIPTION

Figure 1:
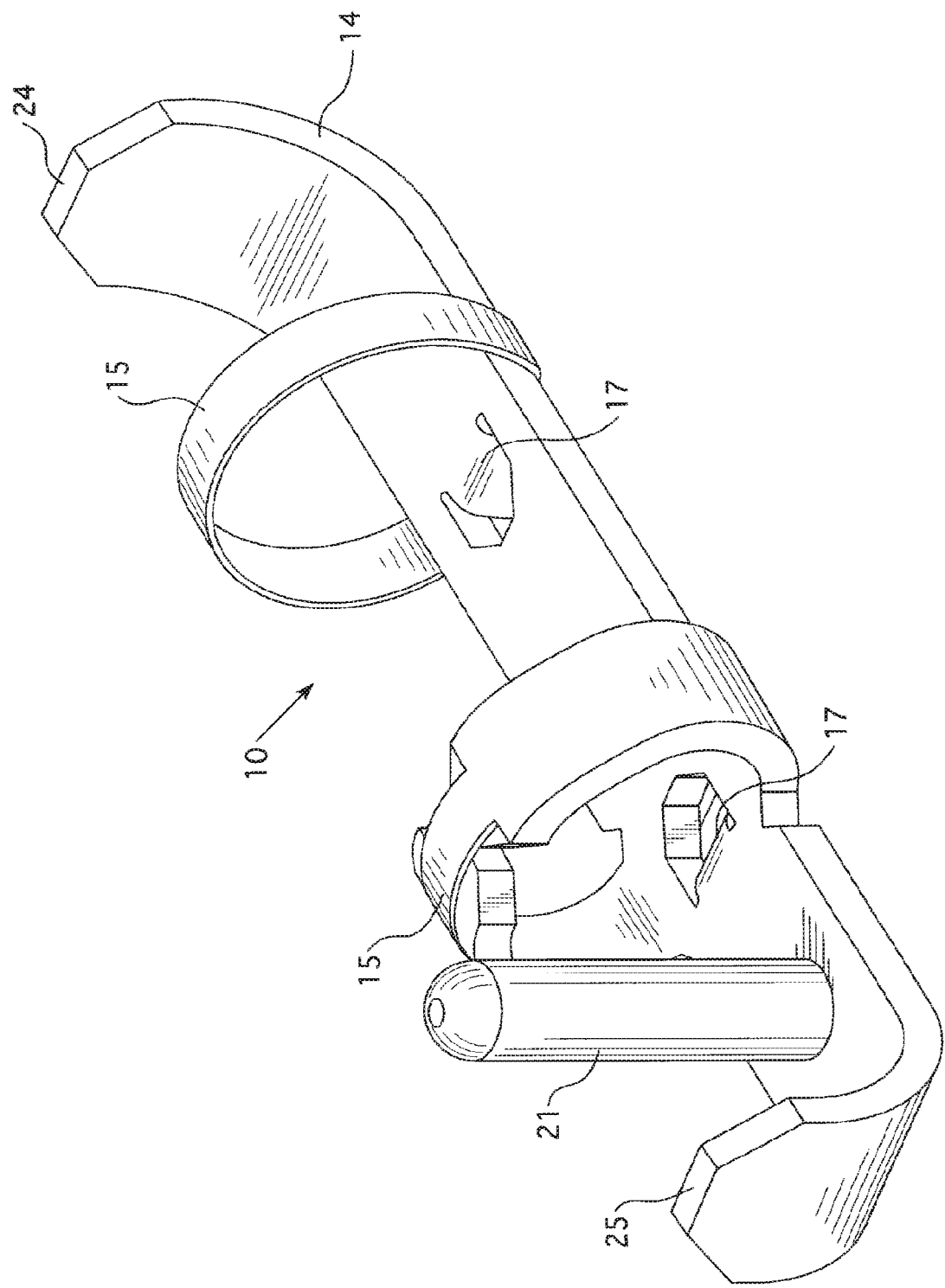
FIG. 1 is a perspective view of the disposable sterile surgical arm support liner for the arm support element of the present invention.
Figure 2:
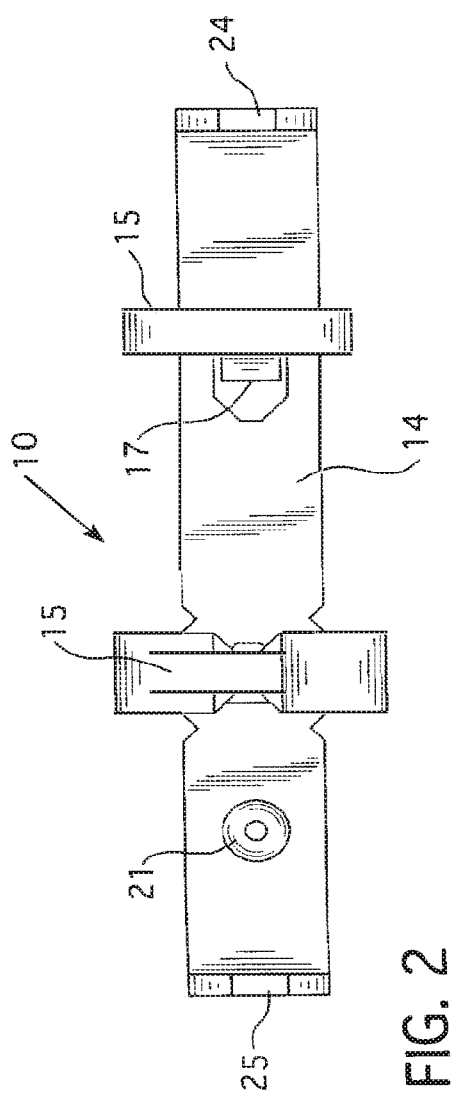
FIG. 2 is a plan view of the support liner illustrated in FIG. 1.
Figure 3:
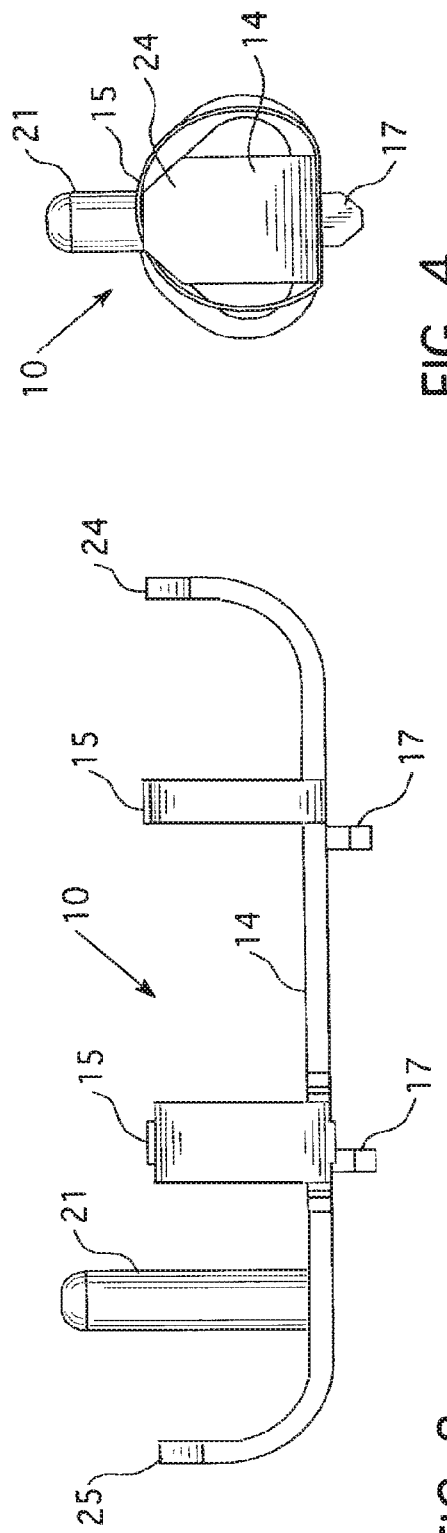
FIG. 3 is a view in side elevation of the support liner shown in FIG. 1.
Figure 4:
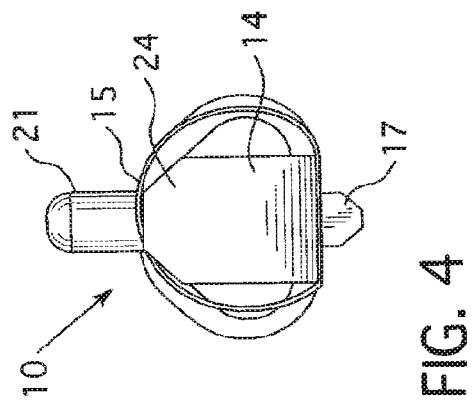
FIG. 4 is a right end view of the support liner shown in FIG. 3.

Referring to the drawings, the disposable sterile arm support liner 10 is used to retain the arm of a patient therein in a sterile condition and to also retain the liner 10 secured to the underlying stainless-steel arm support tray 11. Stainless-steel arm support tray 11 is in turn secured to the distal end of an articulating positioning arm (not shown) of the type, for example, illustrated in U.S. Pat. Nos. 8,028,702 and 8,322,342. It is desirable that such an articulating support arm be adjustable about multiple pivot joints with a single button or lever that unlocks all joints simultaneously, thereby unlocking them and allowing the distal end of the arm to be freely moved about six axes (x,y,z, rotation and translation), and securely fixed anywhere within the operating radius of the device by releasing a button or lever, thereby locking all joints simultaneously and fixing the position of the patient's retained arm.

Such an articulating arm is normally removably attached to the side rail of an operating table using a clamp or clip. The distal end of the articulating arm is provided with a quick release attachment that includes a non-round bore (not shown), which does not allow for rotation, to correspondingly and cooperatively received mounting protrusion 12 in the bottom of stainless-steel arm support tray 11. The mounting protrusion 12 is engaged with a spring-loaded locking clip which transversely engages the annular groove 8 in mounting protrusion 12 when mounting protrusion 12 is pressed into the bore of the distal end of the articulatable support arm. A similar connection is illustrated in U.S. Pat. No. 8,028,702.

Figure 5:
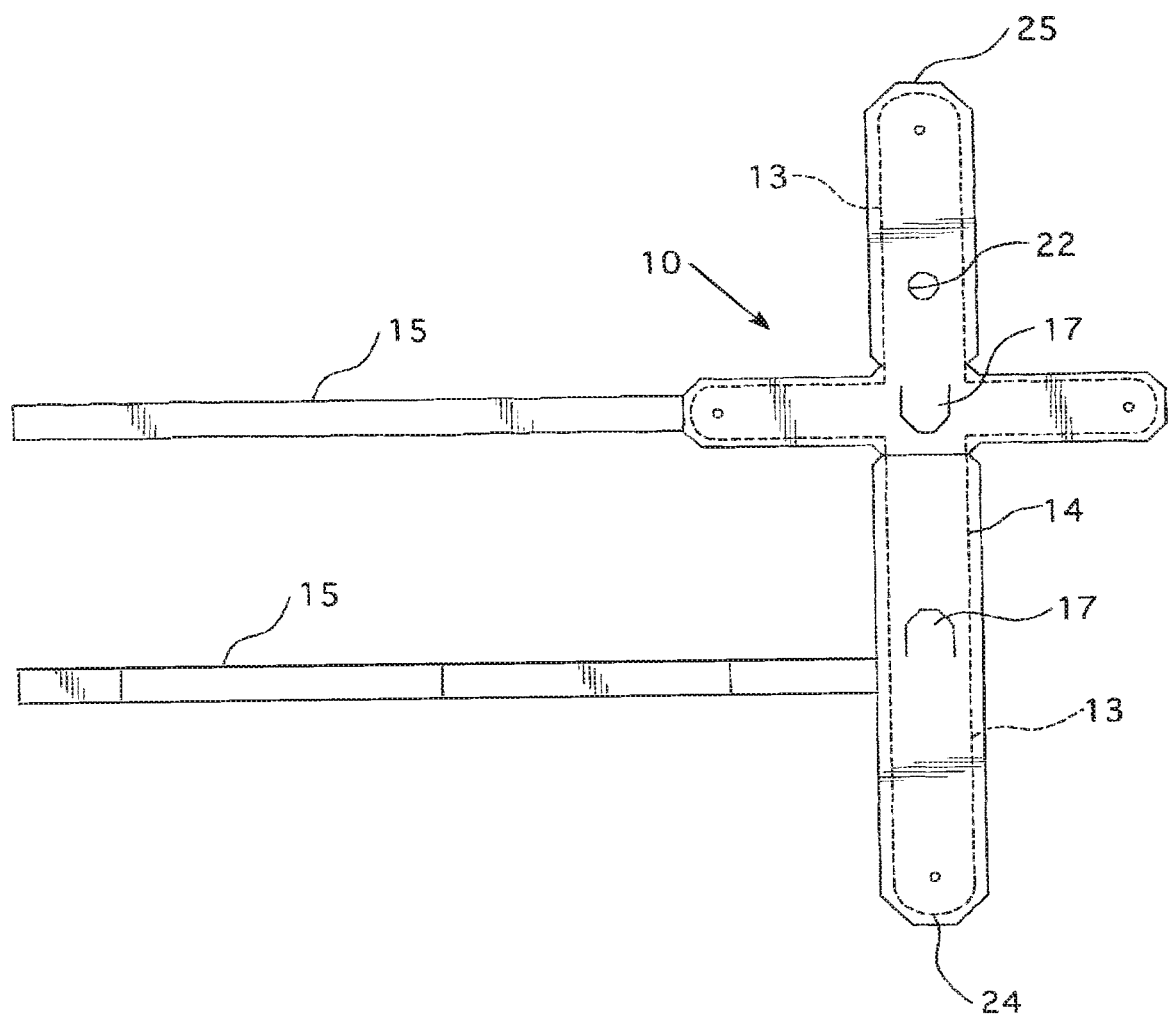
FIG. 5 is a plan view of the disposable arm support liner of FIGS. 1 through 4 illustrated in its original flat configuration prior to being formed and modified to the configuration illustrated in the previous figures.
Figure 6:
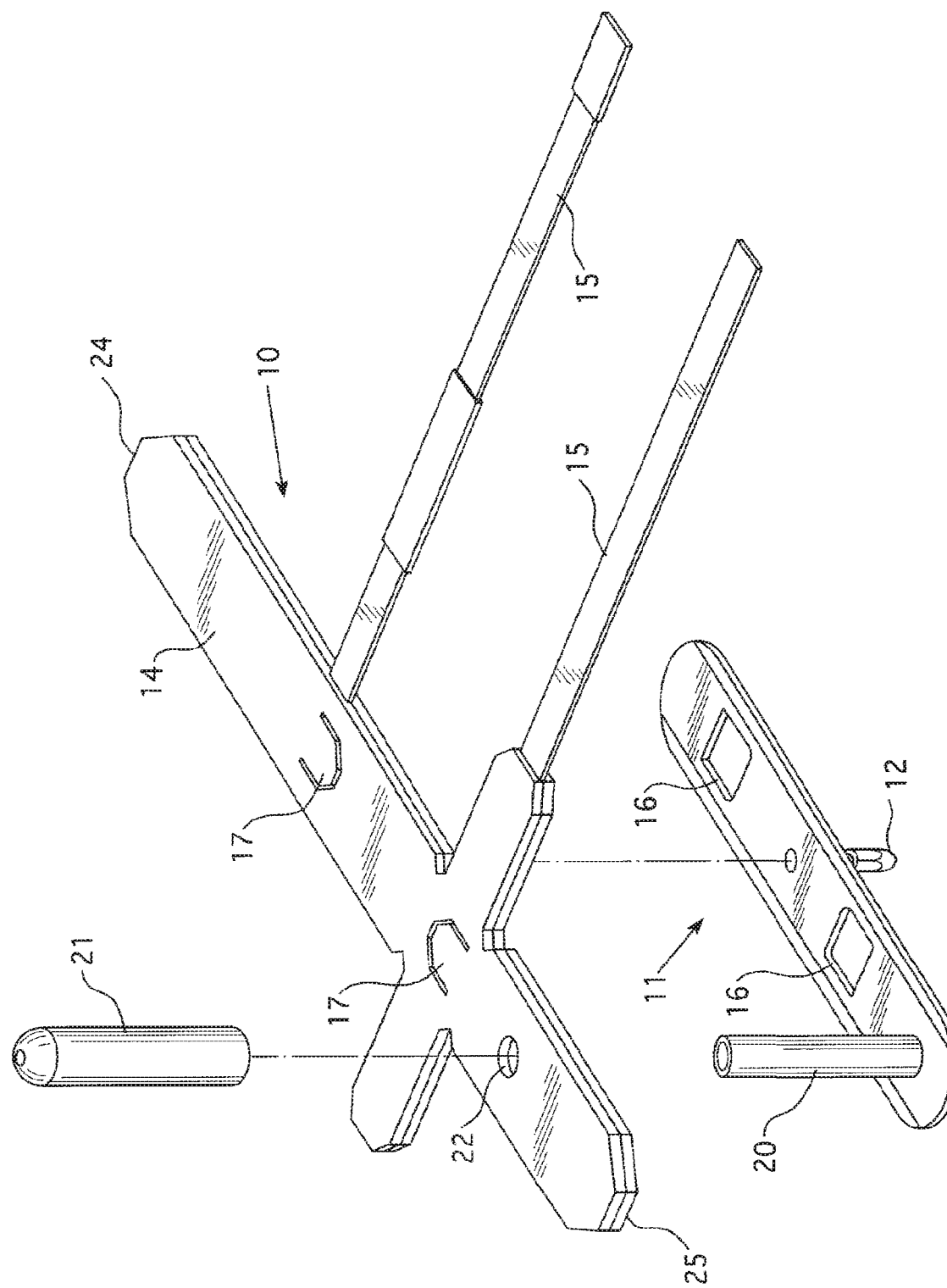
FIG. 6 is an exploded or expanded respective view of the disposable arm support liner shown in its flat pre-used configuration in combination with a stainless-steel arm support tray that is used to support the disposable arm support liner thereby forming the support of the present invention.
Figure 7:
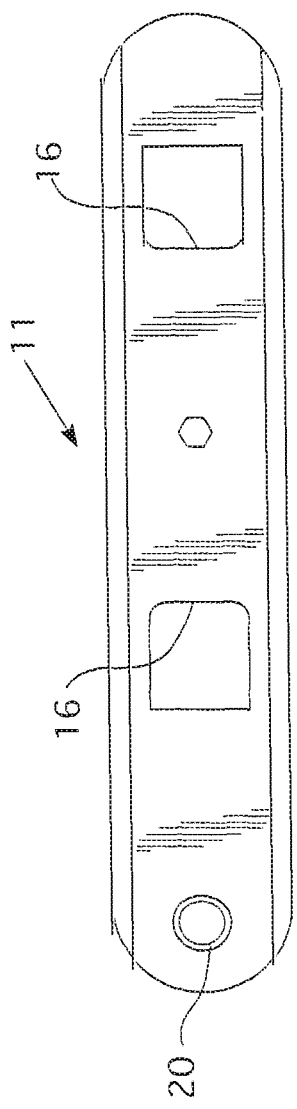
FIG. 7 is a plan view of the stainless-steel arm support tray shown in the bottom portion of FIG. 6.
Figure 9:
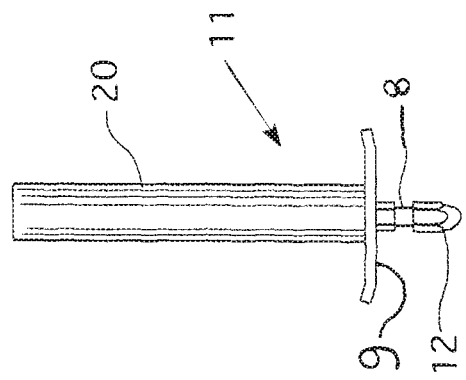
FIG. 9 is a right end view of the arm support tray shown in FIG. 8.
Figure 8:
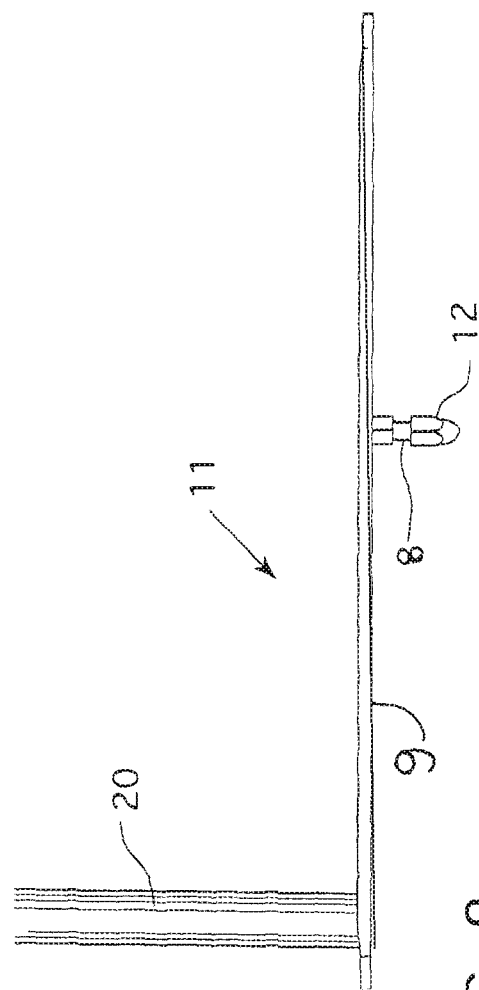
FIG. 8 is a view in side elevation of the arm support tray shown in FIG. 7.
Figure 10:
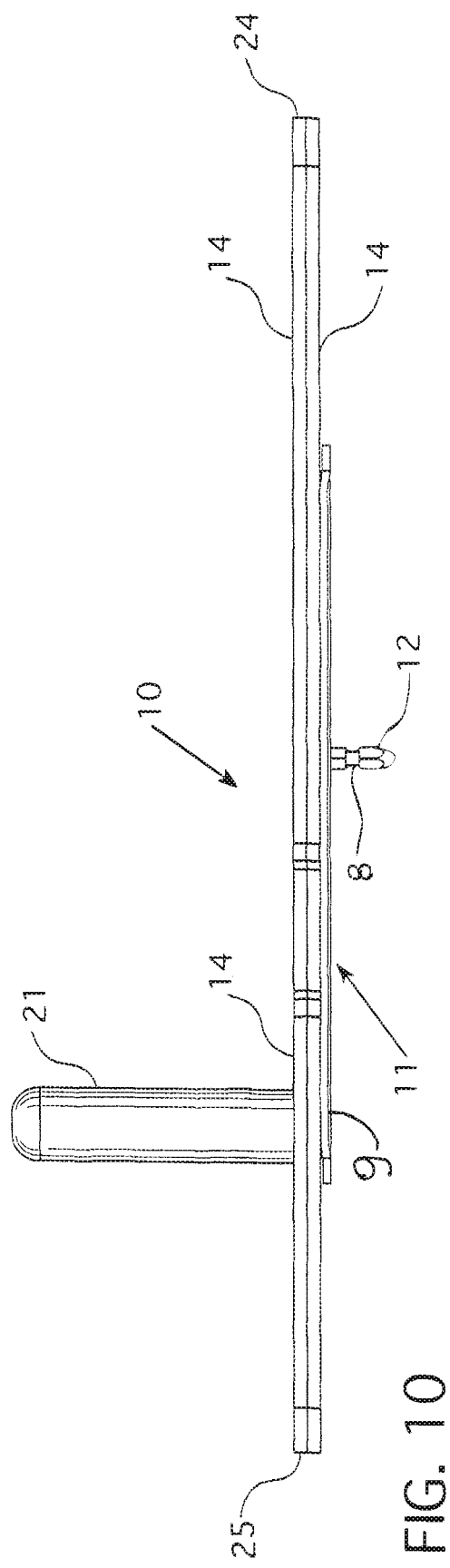
FIG. 10 is a view in side elevation illustrating the disposable arm support liner of the present invention as shown in its flat unused state and secured to the stainless-steel arm support tray.
Figure 11:
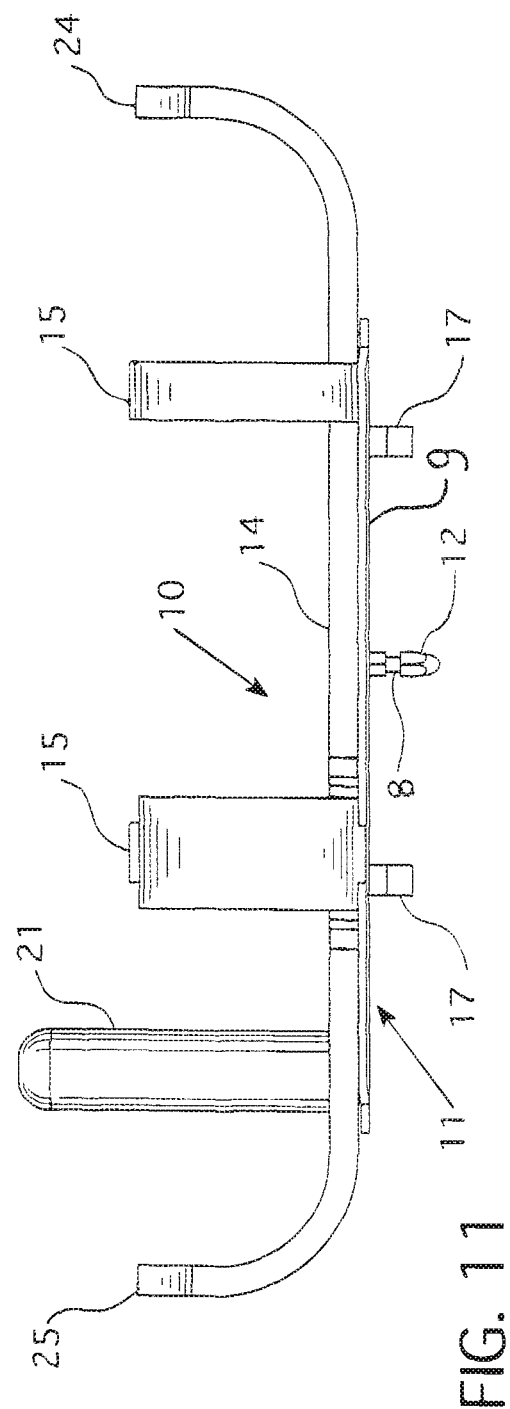
FIG. 11 illustrates the combination shown in FIG. 10 with the disposable malleable support liner being bent or formed and assembled to secure a patient's arm thereto.

The sterile and disposable arm holding or supporting attachment liner 10 consists of a flat malleable material 13, such as lead or aluminum, that is able to be plastically deformed or bent to a new final shape or configuration by hand from a flat configuration as shown in FIGS. 5 and 6, to an arm retaining position with end curvatures as illustrated in FIGS. 1 and 11. The initially flat malleable material 13 is embedded within or laminated by a foam covering 14 whereby any sharp edges or hard surfaces of the malleable material are covered and padded to protect the patient's arm. Adjustable hook and loop straps 15, such as Velcro™, are also secured to the body of the liner 10 in order to allow for tight wrapping of the liner ears around the patient's forearm and wrist in a manner illustrated in FIG. 1.

The stainless-steel arm support tray 11 is provided with a spaced pair of openings 16 which permit locking tabs 17 of liner 10 to be bent downwardly and passed through the apertures provided respectively by openings 16 and then bent therearound and under the supporting tray 11 and against the bottom side 9 of the tray 11, thus firmly securing the sterile disposable arm support liner 10 to the arm support tray 11, which is also usually sterilized.

A vertical post 20 is secured to the tray 11 which provides a post for the patient's hand to wrap around when in position. Post 20 is also protected with a grip cover 21 that is also disposable and sterile. Post 20 maintains the patient's forearm in the proper position.

Vertical post 20 passes through a corresponding aperture 22 provided in liner 10 so that the post 20 is exposed on the upper side of liner 10 and then is covered with the foam post or grip cover 21.

The disposable arm support liner 10 is folded up at its ends behind the elbow at 24 and in front of the hand at end 25 allowing for proper support of the forearm and this also assists in preventing the forearm from sliding.

For additional securement, a secondary wrap may be provided around the patient's arm and secured to the support system by using a sterile elastic self-binding band, such as sold under the trademark Coban™, to further secure the arm.

Accordingly, the sterile disposable arm support liner 10 is attached to the reusable component of the arm holder, namely the sterile stainless-steel arm support tray 11, and the patient's arm is placed on top of the sterile disposable support liner 10. The ends 25 and 24 of the liner 10 would then be bent up in front of the hand and behind the elbow toward the patient's shoulder, thereby creating a rigid cage for support of the patient's arm. Velcro straps 15 would then be tightly wrapped around the patient's arm with the patient's hand wrapped around grip cover 21, further securing the arm to the formed cage, and Coban or similar elastic wrap would then be wrapped around the arm and arm holder, including liner 10 and support tray 11.

The arm holder, including liner 10 and support tray 11, would then have bottom securing protrusion 12 inserted into the bore at the distal end of the articulating arm positioner, thus securely locking the arm holder to the arm positioner.

What is claimed is:

1. An arm retainer for supporting a patient's arm at a desired position on support assembly, the arm retainer comprising:
    a rigid arm tray comprising:
        a connector for connecting the rigid arm tray to the support assembly, and
        an opening for securement of a disposable arm support liner to the rigid arm tray; and
    the disposable arm support liner, comprising:
        a sheet of malleable material with a soft engagement surface, and
        a foldout tab aligned with the opening of the rigid arm tray for securing the disposable arm support liner to the rigid arm tray by folding the foldout tab through the opening and thereafter against the bottom side of the rigid arm tray.

2. The arm retainer of claim 1, wherein the arm support liner has a predetermined cut configuration for wrapping or forming the sheet of malleable material of the arm support liner about a patient's arm for retention.

3. The arm retainer of claim 1, wherein the malleable material comprises at least one of aluminum and lead.

4. The arm retainer of claim 1, wherein the soft engagement surface comprises a plastic sponge foam.

5. The arm retainer of claim 1, comprising a hand grip post extending transversely away from a top side of the tray, wherein the arm support liner comprises a corresponding aperture aligned with the hand grip post for passage of the hand grip post therethrough when the liner is secured to the tray.

6. The arm retainer of claim 5, comprising a disposable tubular plastic sponge sleeve received over the hand grip post.

7. The arm retainer of claim 1, wherein the arm support liner comprises hook and loop straps for securing the arm support liner to the patient's arm.

8. The arm retainer of claim 1, wherein the rigid arm tray comprises stainless steel.

9. The arm retainer of claim 1, wherein the connector comprises an annular groove configured to transversely engage with a locking clip of the support assembly.

10. The arm retainer of claim 1, wherein the connector is configured to engage an opening that substantially prevents rotation of the rigid arm tray with respect to the support assembly when the rigid arm tray is connected to the support assembly.

11. A method for supporting a patient's arm at a desired position on support assembly utilizing an arm retainer, the method comprising:
    connecting a rigid arm tray of the arm retainer to the support assembly;
    aligning a foldout tab of a disposable arm support liner comprising a sheet of malleable material and a soft engagement surface, with an opening of the rigid arm tray; and securing the disposable arm support liner to the rigid arm tray by folding the foldout tab through the opening of the rigid arm tray and, thereafter, against the bottom side of the rigid arm tray.

12. The method of claim 11, further comprising retaining the patient's arm within the disposable arm support liner by forming the sheet of malleable material of the arm support liner about the patient's arm.

13. The method of claim 11, wherein the malleable material comprises at least one of aluminum and lead.

14. The method of claim 11, wherein the soft engagement surface comprises a plastic sponge foam.

15. The method of claim 11, wherein securing the disposable arm support liner to the rigid arm tray further comprises passing a hand grip post, extending transversely away from a top side of the tray, through a corresponding aperture in the arm support liner that is aligned with the hand grip post.

16. The method of claim 15, comprising receiving a disposable tubular plastic sponge sleeve over the hand grip post.

17. The method of claim 11, comprising securing the arm support liner to the patient's arm utilizing hook and loop straps of the arm support liner.

18. The method of claim 11, wherein the rigid arm tray comprises stainless steel.

19. The method of claim 11, wherein connecting the rigid arm tray to the support assembly comprises transversely engaging a locking clip of the support assembly with a mounting protrusion of the rigid arm tray.

20. The method of claim 11, comprising substantially preventing rotation of the rigid arm tray with respect to the support assembly when the rigid arm tray is connected to the support assembly.

\* \* \* \* \*